(12) United States Patent
Horbaschek et al.

(10) Patent No.: US 6,404,850 B1
(45) Date of Patent: Jun. 11, 2002

(54) CARDIOANGIOGRAPHY APPARATUS

(75) Inventors: Heinz Horbaschek; Johann Seissl, both of Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/665,811

(22) Filed: Sep. 20, 2000

(30) Foreign Application Priority Data

Sep. 20, 1999 (DE) .......................................... 199 44 982

(51) Int. Cl.⁷ ................................................. H05G 1/10
(52) U.S. Cl. ............................................ 378/95; 378/98.2
(58) Field of Search .................................. 378/95, 98.2

(56) References Cited

U.S. PATENT DOCUMENTS 5,054,045 A * 10/1991 Wheteng et al. .......... 378/98.2
5,630,414 A    5/1997 Horbaschek et al.

FOREIGN PATENT DOCUMENTS

DE          43 28 282         3/1995

OTHER PUBLICATIONS

"Quantitative Coronary and Left Ventricular Cineangiography Methodology and Clinical Applications" Reiber et al (1986), pp. 190–195.

* cited by examiner

*Primary Examiner*—Craig E. Church
(74) *Attorney, Agent, or Firm*—Schiff Hardin & Waite

(57) ABSTRACT

An x-ray diagnostic system, particularly for cardioangiography, has an x-ray and an x-ray image intensifier/video chain or other x-ray image converters, with the x-ray and the x-ray image intensifier being cyclically moved during the production of a number of successive images. The motion of the vessel due to the heartbeat is compensated with a cardiac motion compensation unit in a small image region having an abnormality to be investigated, particularly a stenosis.

4 Claims, 2 Drawing Sheets

CARDIOANGIOGRAPHY APPARATUS

BACKGROUND OF THE INVENTION

1. Field of the Invention

The present invention is directed to an x-ray diagnostic apparatus, particularly for cardioangiography, having an x-ray source and an x-ray image intensifier/video chain or other x-ray image converters, wherein the x-ray source and the x-ray image intensifier are cyclically moved during the production of a number of successive images.

2. Description of the Prior Art

An x-ray diagnostic apparatus of this type is disclosed, for example, by German PS 44 13 458, wherein difference images are produced in the pathfinder technique for better spatial visibility in certain device settings, with the x-ray diagnostic apparatus being is cyclically moved.

"dynavision" exposure series is usually made of a resting subject during a contrast agent injection for the currently standard 3D reconstruction of angio systems, with an exposure series over an angular range of ≧180° of the subject ensuing by means of a rotating C-arm.

A 3D reconstruction of the selected subject region ensues from this series according to a specific reconstruction algorithm.

The desired view can then be selected for observation with the assistance of various presentation modes, for example MIP (maximum intensity projection) or VR (volume rendering).

A prerequisite for a successful 3D reconstruction is that the subject be at rest and, in the case of angiography, an adequately long and uniform contrast agent display, so that such 3D angiography reconstructions can currently be employed only for the presentation of vessels in the skull.

However, it would also be diagnostically important to be able to portray vessels with greater movement in angio systems with 3D reconstruction, particularly coronary arteries, wherein it is especially the morphology, i.e. the anatomical modifications, for example of a stenosis, that are of critical diagnostic significance.

At first glance, however, it would seem a 3D reconstruction is practically impossible in cardioangiography. The heartbeat constantly changes the position of the vessels in the x-ray image, so that—purely theoretically—the exposures for the dynavision scene could only be made given EKG-triggered image sequence control and an extremely long bolus, which, however, is completely out of the question for health reasons.

SUMMARY OF THE INVENTION

An object of the present invention is to provide an x-ray diagnostic apparatus of the type initially described which can also be utilized in cardioangiography.

For achieving this object, it is inventively provided that the motion of the vessel due to the heartbeat is compensated with a "cardiac motion compensation" in a small image region having an abnormality to be investigated, particularly a stenosis.

An important, basic idea of the invention is the limitation of the 3D reconstruction to an extremely small image region, namely specifically that of the stenoses, i.e. of the constrictions of the vessels. In an embodiment of the invention, the vessel is acquired in the selected, small image excerpt by a center line detection and is retained on a point of the image. Views of the stenosis thus arise from different observation angles dependent on the respective position of the C-arm in the dynavision, rotational movement.

The further-processing and the 3D reconstruction have an especially simple form when the vessel acquired by the center line detection and retained on a point of the image is "bent straight" by a computer in the retained image excerpt, so that a 3D reconstruction of the selected image area from the digitized data of successive images of an image sequence only ensues subsequently with a reconstruction algorithm.

It is within the scope of the invention for this central region of the image to be employed as a virtual isocenter for the 3D reconstruction. A geometrical distortion correction (x-ray image intensifier, beam path, etc.) is eliminated since the image region is extremely small. At the end of the calculation, the image region with the stenosis as a 3D image is available as an image result and provides information about the existing morphology. A better estimate of the therapeutic measures is thus possible, for example balloon angioplasty, laser treatment, bypass operation, etc.

DESCRIPTION OF THE PREFERRED EMBODIMENTS

Figure 1:
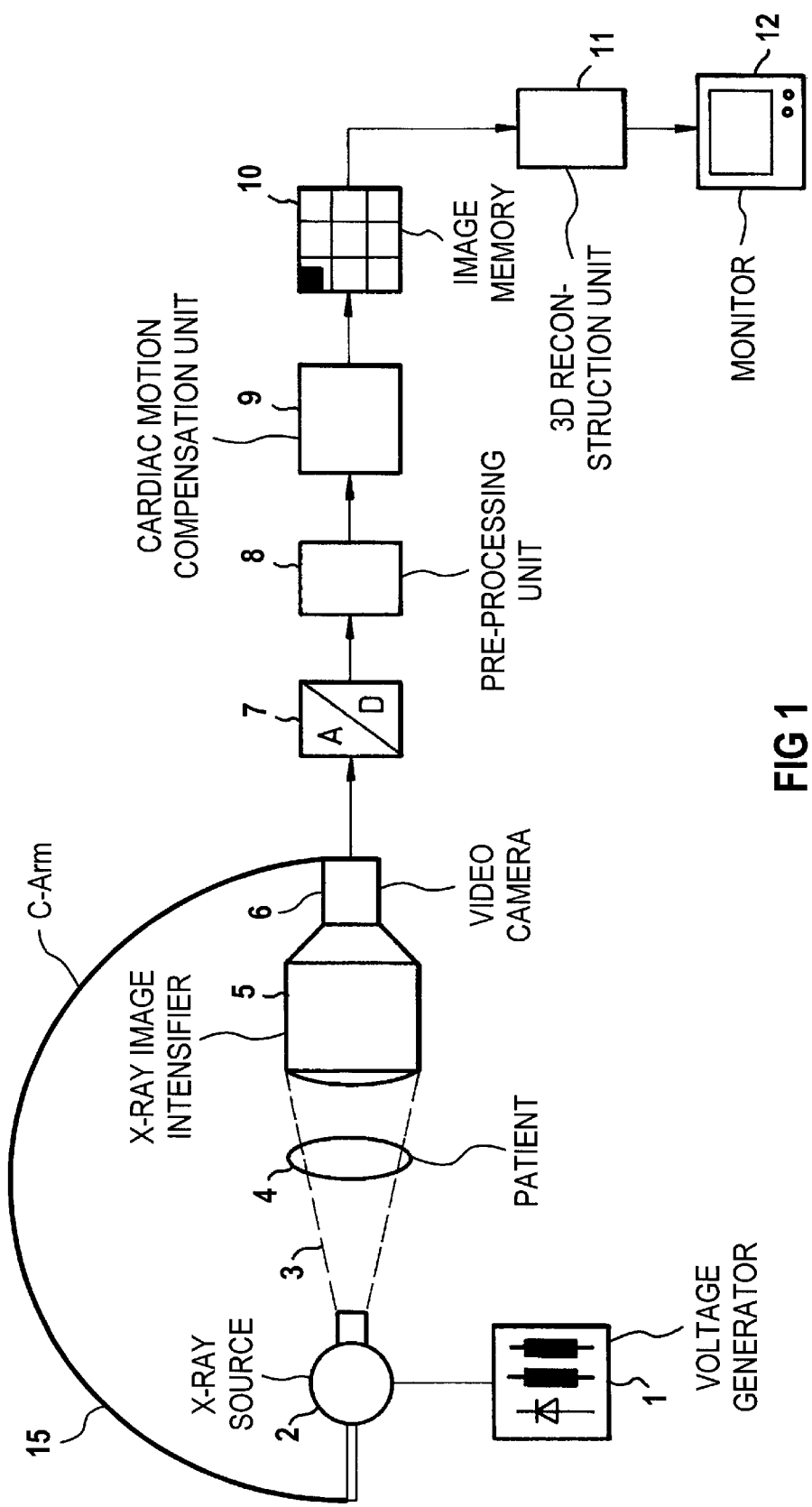
FIG. 1 is a block diagram of an inventive x-ray diagnostic apparatus.

FIG. 1 shows an inventive x-ray diagnostic apparatus with a high-voltage generator 1 that feeds an x-ray tube 2 in whose beam path 3 the patient 4 is located. An x-ray image intensifier 5 following in the beam path 3 is coupled to a video camera 6 whose output signal is supplied to an analog-to-digital converter (A/D converter) 7. The x-ray tube 2 and the x-ray image intensifier 5 are rotated around the patient 4 in a known manner by a C-arm 15. As warranted, the digitalized video signal is supplied via a pre-processing unit 8 to a cardiac motion compensation unit 9, which alternatively can follow the image memory 10. The cardiac compensation motion compensation unit 9 undertakes a center line detection and a "straightening" of the bent, small image excerpts of a vessel with a stenosis. A 3D reconstruction unit 11 undertakes a 3D reconstruction of the selected image region with a reconstruction algorithm from the various images that have been acquired during a rotation of the C-arm 15 of the x-ray system. The desired image region and the desired view then can be displayed in the monitor 12.

Figure 2:
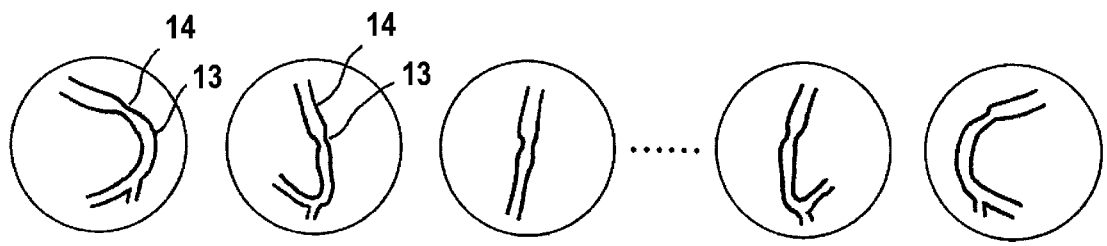
FIG. 2 shows a series of dynavision exposures of a small vessel region with a stenosis having the displacements and bends due to the heartbeat.
Figure 3:
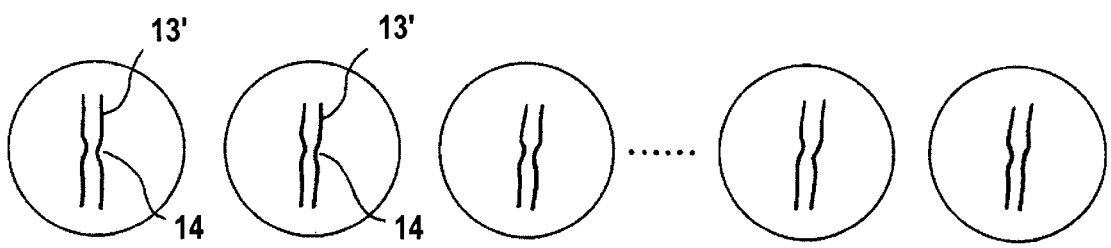
FIG. 3 is a reproduction of the processed images according to FIG. 2 following a "cardiac motion compensation" and a straightening of the vessel excerpt in accordance with the invention.
Figure 4:
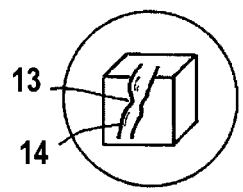
FIG. 4 is a schematic "small area" 3D reconstruction of the selected image excerpt.

The vessel excerpt 13 with the stenosis 14 to be detected in greater detail can be seen in FIGS. 2–4. Whereas, due to the heartbeat, the vessel excerpt exhibits a different position and shape in every image in the image series of FIG. 2 that was acquired in the dynavision, the vessel excerpt 13' as well as the stenosis 14 contained therein are converted into a form after the motion compensation by center line detection and straightening of the vessel excerpt 13' so that it looks like a dynavision exposure in sequence given vessels at rest, for example in the skull.

A "small area" 3D reconstruction of the vessel 13 and of the stenosis 14, as schematically shown in FIG. 4, is produced from the computationally converted image series according to FIG. 3 in the 3D reconstruction unit 11, whereby the respective view of this 3D image can be selected by the user.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostic apparatus for cardioangiography, comprising:

an x-ray source which emits an x-ray beam which is adapted to penetrate a subject having a beating heart;

an x-ray detector on which x-rays are incident after penetrating said examination subject, said x-ray detector generating electrical signals corresponding to the x-rays incident thereon;

an image processing arrangement for producing a visible image from said electrical signals;

a mount for said x-ray source and a said radiation detector for cyclically moving said x-ray source and said radiation detector during production of a plurality of successive images including a vessel exhibiting motion due to heartbeats; and a cardiac motion compensation unit which supplies a signal to said image processing arrangement representing only a selected small region of each of said plurality of successive images to compensate for motion of said vessel in said selected small region due to heartbeats.

2. An x-ray diagnostic apparatus as claimed in claim 1 wherein said image processing arrangement is a 3D reconstruction unit which generates a 3D image of said cardiac motion compensation unit selects a small image region of said plurality of images, selected by said cardiac motion compensation unit, by center line detection, with said vessel being retained on a point of said image.

3. An x-ray diagnostic apparatus as claimed in claim 2 wherein said 3D reconstruction unit converts said vessel being retained on a point of said image into a straightened display.

4. An x-ray diagnostic apparatus as claimed in claim 1 wherein each of said plurality of images has a central image region, and wherein said image processing arrangement is a 3D reconstruction unit forms a virtual isocenter at said central image region for three-dimensional reconstruction of said selected image region using a reconstruction algorithm from said plurality of successive images.

* * * * *